United States Patent
Nevels et al.

(10) Patent No.: US 8,945,032 B2
(45) Date of Patent: Feb. 3, 2015

(54) ORTHOSIS SUPPORT

(75) Inventors: Daniel W. Nevels, Dayton, OH (US); E. Veronica Nevels, Dayton, OH (US)

(73) Assignee: Innovative Accessory Products, Inc., Dayton, OH (US)

( * ) Notice: Subject to any disclaimer, the term of this patent is extended or adjusted under 35 U.S.C. 154(b) by 561 days.

(21) Appl. No.: 12/830,014

(22) Filed: Jul. 2, 2010

(65) Prior Publication Data

US 2012/0004585 A1    Jan. 5, 2012

(51) Int. Cl.
*A61F 5/00* (2006.01)
*A45F 3/14* (2006.01)
*A41F 3/02* (2006.01)
*A61F 5/01* (2006.01)
*A61F 5/37* (2006.01)

(52) U.S. Cl.
CPC ............... *A61F 5/0123* (2013.01); *A61F 5/013* (2013.01); *A61F 5/373* (2013.01)
USPC .................................. 602/19; 224/250; 2/338

(58) Field of Classification Search
USPC .......... 128/846, 869, 870, 876, 875; 119/172; 602/4, 1; 224/226, 148, 223, 253, 250, 224/242, 224, 151; 2/323, 311–319, 338
See application file for complete search history.

(56) References Cited

U.S. PATENT DOCUMENTS

| | | | |
|---|---|---|---|
| 569,511 A | 10/1896 | McClung, Jr. | |
| 1,097,070 A | 5/1914 | Anderson | |
| 1,548,711 A * | 8/1925 | Cooper | 602/25 |
| 2,553,007 A * | 5/1951 | Rosenthal | 5/424 |
| 4,252,112 A * | 2/1981 | Joyce | 602/26 |
| 4,337,883 A * | 7/1982 | Pate | 224/250 |
| 4,531,515 A | 7/1985 | Rolfes | |
| 4,728,553 A * | 3/1988 | Daniels | 428/100 |
| 5,256,119 A * | 10/1993 | Tudor | 482/74 |
| 5,437,402 A * | 8/1995 | Ring | 224/159 |
| 5,551,447 A * | 9/1996 | Hoffman et al. | 128/869 |
| 7,066,181 B2 * | 6/2006 | West | 128/875 |
| 7,300,410 B1 * | 11/2007 | Weber | 602/4 |
| 7,473,235 B2 | 1/2009 | Schwenn et al. | |
| 2002/0068667 A1 * | 6/2002 | Strachan | 482/124 |
| 2003/0130098 A1 * | 7/2003 | Marco | 482/124 |
| 2004/0181852 A1 * | 9/2004 | Cogswell | 2/313 |
| 2005/0192159 A1 | 9/2005 | Jackson et al. | |
| 2006/0293631 A1 | 12/2006 | Bolt | |
| 2008/0125685 A1 * | 5/2008 | Bernardoni | 602/32 |

FOREIGN PATENT DOCUMENTS

GB    2136294 A * 9/1984 ............... A61F 5/01

* cited by examiner

*Primary Examiner* — Patricia Bianco
*Assistant Examiner* — Tarla Patel
(74) *Attorney, Agent, or Firm* — Thompson Hine LLP (57) ABSTRACT

An orthosis support is disclosed that includes a belt having a connector to close the belt in a continuous loop, a belt attachment member receiving the belt, and a strap extending from the belt attachment member. The strap has a first end and a second end and is closable as a loop with at least one of the first and second ends releasably connectable to the strap itself.

12 Claims, 6 Drawing Sheets

ORTHOSIS SUPPORT

FIELD OF THE INVENTION

The present invention relates generally to a support for an orthosis device, in particular to a belt and strap support for holding the orthosis device in place.

BACKGROUND

Orthosis devices are routinely worn by a wearer to modify, support, align, prevent, replace, or correct bodily deformities/injuries or to improve or assist the functions of body structures of the neuromuscular and skeletal systems. Typically the orthosis is applied to the outside of the body. The orthosis can align the body and the limbs or effect motion by assisting, resisting, blocking, or unloading the body weight.

Not all orthosis devices, however, fit each individual patient perfectly. In fact, some orthoses are prone, upon movement of the body or limb, to slide out of place. For example, walking may cause a knee brace or elbow brace to slip or slide.

SUMMARY

One aspect for supporting an orthosis is disclosed herein, which is identified as an orthosis support. The disclosed orthosis supports may include a belt having a connector to close the belt in a continuous loop, a belt attachment member receiving the belt, and a strap extending from the belt attachment member. The strap has a first end and a second end and is closable as a loop with at least one of the first and second ends releasably connectable to the strap itself. The strap is positionable to loop about at least one component of an orthosis to support the orthosis in a preselected position on a wearer.

In one embodiment, the belt attachment member is movable, preferably slidable, along the belt and includes a belt entrance and a belt exit for receiving the belt on/through the belt attachment member. The belt attachment member has a longitudinal axis, and the belt entrance and belt exit may be slots that are generally parallel to the longitudinal axis. In one embodiment, the longitudinal axis divides the belt attachment member into two portions with the first portion having the belt entrance and the second portion having the belt exit. The two portions may be mirror images of one another.

The belt attachment member also includes a strap passage, such as a slot that the strap passes through. In one embodiment, the slot may be oriented generally perpendicular to the belt entrance and belt exit. In another embodiment, the belt attachment member may include a sleeve that defines the strap passage rather than a slot. The strap passage defined by the sleeve may be aligned with the longitudinal axis of the belt attachment member.

In one embodiment, the strap has a first end and a second end that are both releasably connectable to the strap itself. When the first and second ends are releasably connected to the strap, a closed, continuous loop is formed. The first end and the second ends both include releasable attachment members and the segment of the strap between the first and second ends includes first and second mating releasable attachment members positionable to mate with the first end and the second end, respectively.

DETAILED DESCRIPTION

The following detailed description will illustrate the general principles of the invention, examples of which are additionally illustrated in the accompanying drawings. In the drawings, like reference numbers indicate identical or functionally similar elements.

Figure 1:
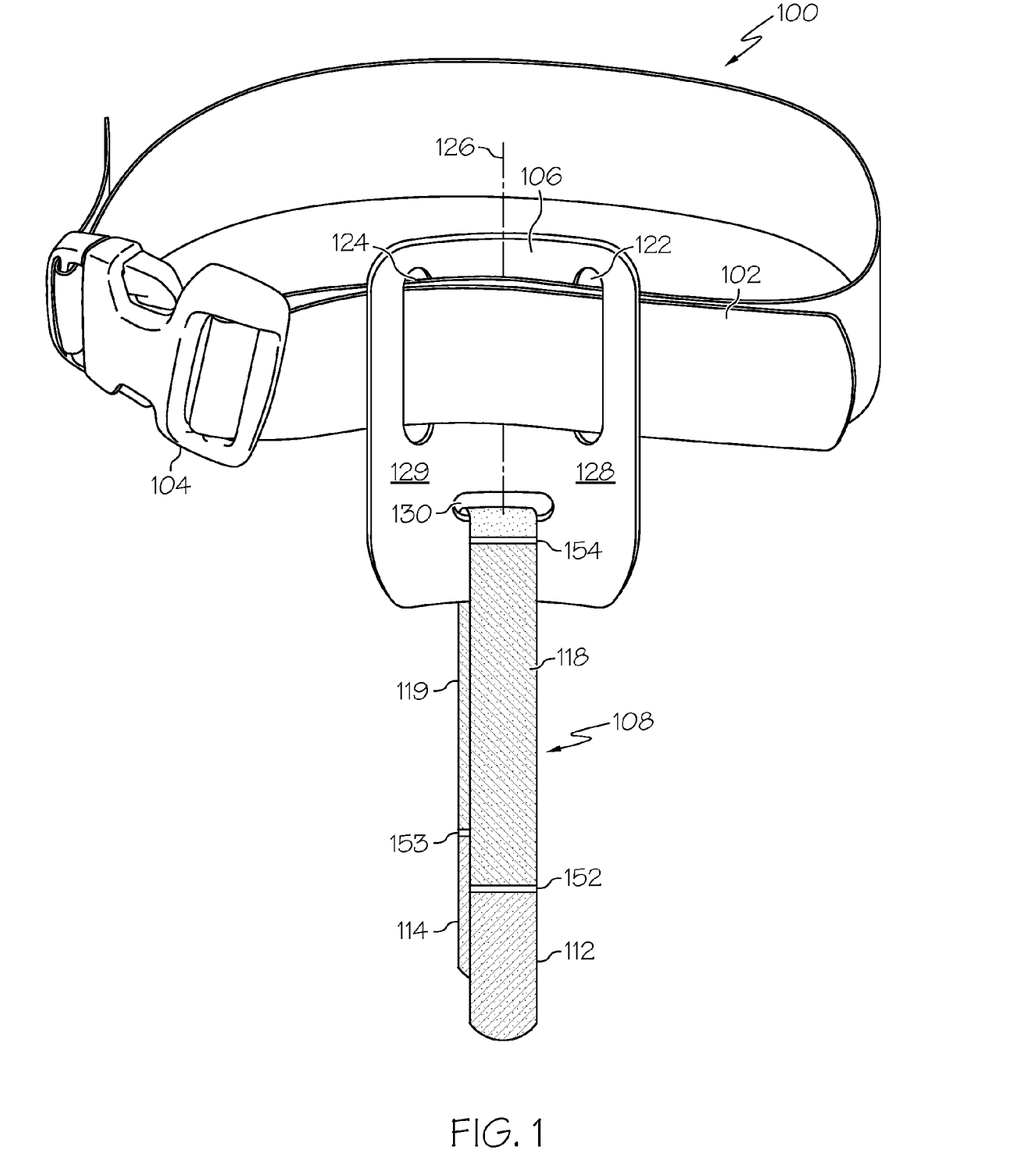
FIG. 1 is a front perspective view of one embodiment of an orthosis support having an open strap.

Referring to FIG. 1, an orthosis support, generally designated 100, is shown that includes a belt 102 having a connector 104 to close the belt, a belt attachment member 106 receiving the belt 102, and a strap 108 extending from the belt attachment member 106. The strap 108 has a first end 112 and a second end 114. At least one of the first end 112 and the second end 114 are connectable to the strap 108 itself to form a closed loop. The strap 108, as shown in FIGS. 7-9, is positionable to loop about at least one component 302, 302', 402 of an orthosis 300, 300', 400 and is closed upon itself to support the orthosis.

Figure 7:
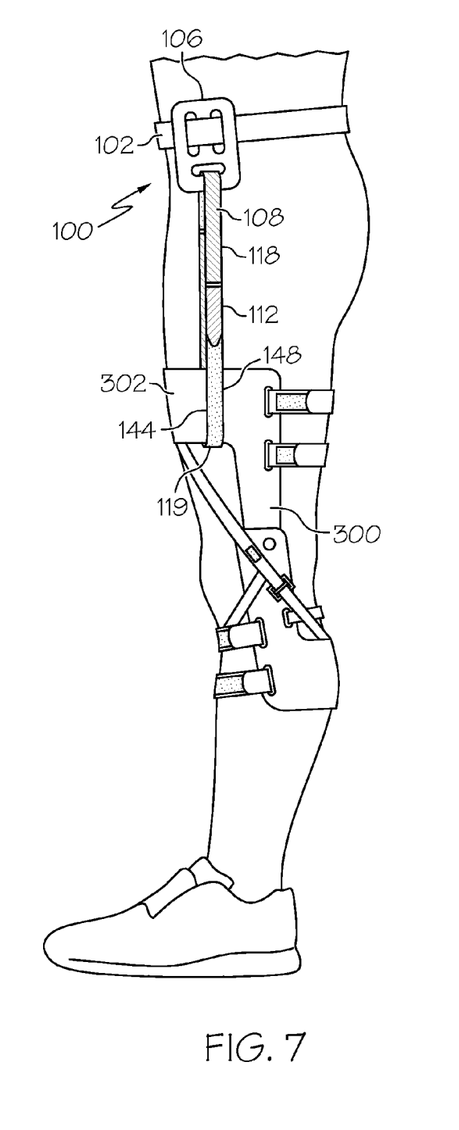
FIG. 7 is a side perspective view of a person having a knee brace supported by one embodiment of the orthosis support of FIG. 1.
Figure 8:
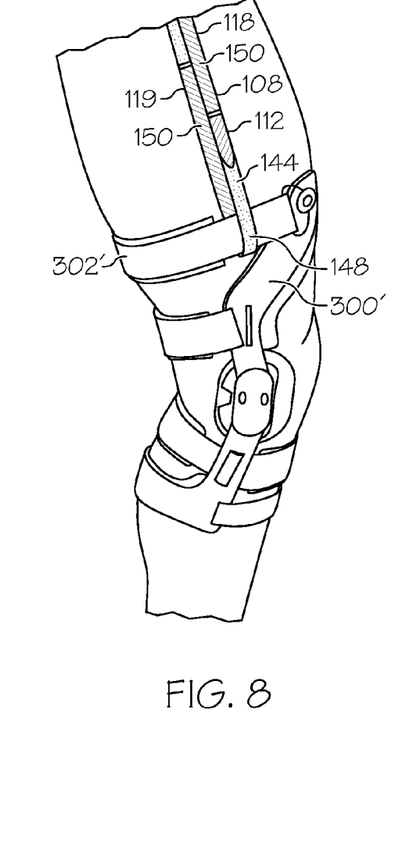
FIG. 8 is a side perspective view of a leg of a person having an alternate knee brace supported by the strap of one embodiment of an orthosis support.
Figure 9:
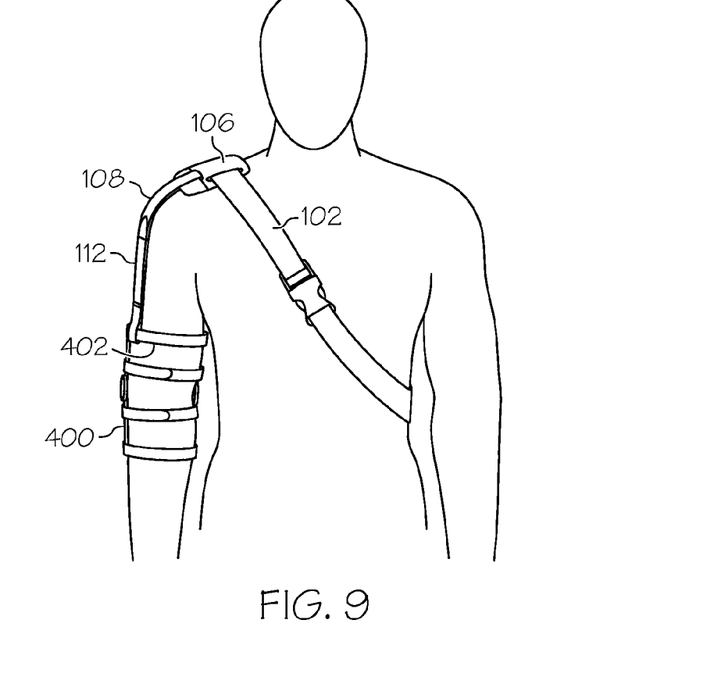
FIG. 9 is a front perspective view of the torso and arm of a person having an elbow brace supported by one embodiment of an orthosis support.

As illustrated in FIGS. 7-8, the orthosis may be a knee brace 300, 300' or, as illustrated in FIG. 9, may be an elbow brace. The orthosis support 100 is adjustable to support the respective orthoses 300, 300', 400 in a preselected position. The position chosen is preferably the position that will maximize the function of the orthosis. The strap 108 may loop under, over, or around a component 302, 302', 402 of the orthoses and be releasable closed by connection to itself by one or both of the first and second ends 112, 114. As such, the orthosis support 100 supports the particular orthosis such that slipping and sliding of the orthosis into an undesired position is reduced or eliminated. While the orthoses 300, 300', 400 are illustrated as a knee brace and an elbow brace, the invention is not limited thereto. One of skill in the art will appreciate that the belt 102 and belt attachment member 106 may be shaped and configured in alternate embodiments for placement on a wearer in locations other than the waist show in FIG. 7 and the diagonal orientation about the torso shown in FIG. 9.

Referring to FIG. 1 in more detail, the belt 102 is adjustable to varying lengths such that the belt may be adjusted to fit the wearer. The connector 104 of the belt 102 may be a buckle, a snap, a plastic clasp, or the like to secure the belt in a closed orientation about the wearer. The material for construction of the belt 102 is not limited. The material should be selected to provide adequate support to the belt attachment member 106 to maintain the support provided to the orthosis.

Figure 5:
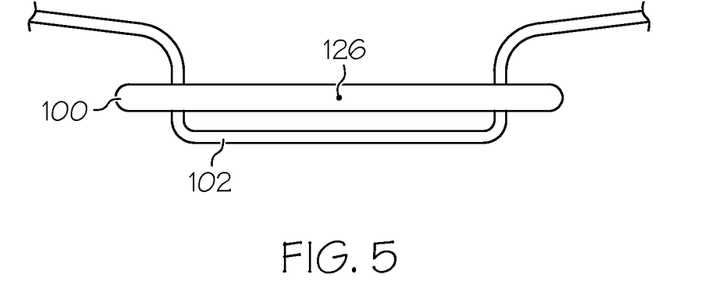
FIG. 5 is a top view of one embodiment of a belt attachment member having a belt therethrough.
Figure 6:
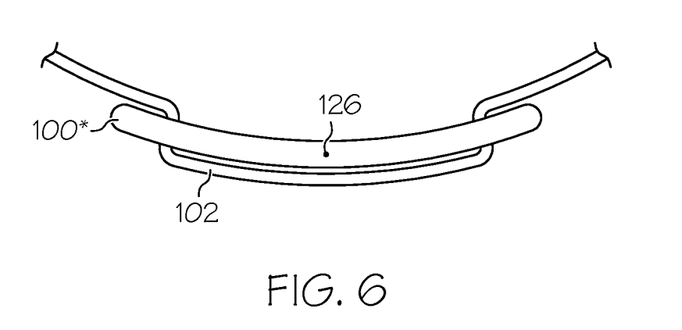
FIG. 6 is a top view of an alternate embodiment of a belt attachment member having a belt therethrough.

The belt attachment member 106 is movable along the belt 102, preferably, generally slidable along the belt 102. In one embodiment, the belt attachment member 106 is a generally plate-like, generally rectangular member, as best seen in FIG. 5. In another embodiment, the belt attachment member 106 is a generally curvilinear, generally rectangular member, as best seen in FIG. 6.

In order to receive the belt 102, the belt attachment member 106 has a belt entrance 122 and a belt exit 124 therein. The belt entrance 122 and belt exit 124 are positioned in the belt attachment member 106 such that they are both generally parallel with a longitudinal axis 126 of the belt attachment member 106. The longitudinal axis 126 may divide the belt attachment member 106 into two portions 128, 129, where the first portion 128 includes the belt entrance 122 and the second portion 129 includes the belt exit 124. In one embodiment, the first portion 128 and the second portion 129 are mirror images of one another.

The belt entrance 122 and belt exit 124 may both be slots through the belt attachment member 106. The slots may be dimensionally larger than the width and thickness of the belt 102. Such dimensions of the slots can enable the belt attachment member 106 to be movable or slidable on the belt 102.

The belt attachment member 106 is not particularly limited to being constructed of or including a particular material. In one embodiment, the belt attachment member 106 may be leather. In another embodiment, the belt attachment member 106 may be plastic. The plastic may be rigid or flexible. The plastic may be thermoplastic resin, but is not limited thereto. Some suitable example thermoplastic resins include homopolyethylene resins, ethylene copolymer resins, homopolypropylene resins, propylene-α-olefin copolymer resin, homo-polystyrene resin, polystyrene resin including rubber-like material, acrylon nitrile butadiene styrene resin ("ABS"), acrylonitrile-styrene resins, AAS (ASA) resin, AES resin (weather and impact strength resin), syndiotactic polystyrene resin. In one embodiment, the belt attachment member 106 is constructed of or includes an ABS thermoplastic resin. It can be advantageous, but is not required, for the belt attachment member 106 to be flexible so that it can conform to the contours of the portion of the wearer where it is positioned. However, the flexibility of the belt attachment member 106 should be such that it still provides consistent support to the orthosis.

The belt attachment member 106 may be about 2 in to about 6 in wide, preferably about 3 in to about 4 in wide, and about 3 in to about 7 in long, preferably about 4 in to about 5 in long, and may be about ⅛ in to about ¼ in thick. While these dimensions are advantageous to provide a belt attachment member 106 that is not too cumbersome or bulky to the wearer, the dimension of the belt attachment member 106 are not to be construed as limited thereto.

Figure 2:
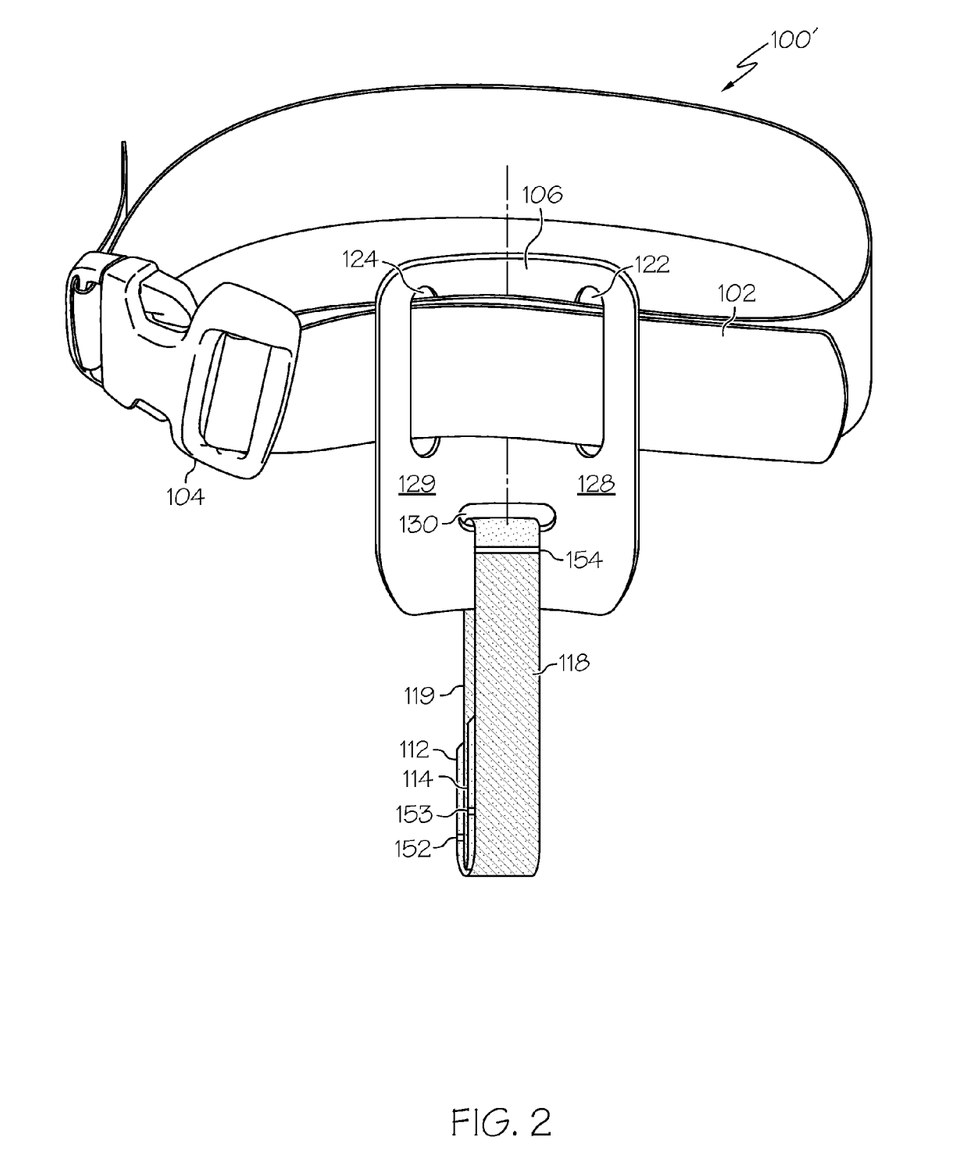
FIG. 2 is a front perspective view of one embodiment of an orthosis support having a closed strap.

The belt attachment member 106 also includes a strap passage 130 for the strap 108 to pass through the belt attachment member 106. In one embodiment, the strap passage 130 is a slot passing through the belt attachment member 106. The strap 108 may loop through the slot and be releasably closed upon itself to form a loop as shown in FIG. 2 or may lie open as shown in FIG. 1. The loop of strap 108 shown in FIG. 2 is considered to be a continuous loop even though it has a first end 112 and a second end 114. In one embodiment, the strap passage 130 may be oriented generally perpendicular to the belt entrance 122 and belt exit 124.

Figure 10:
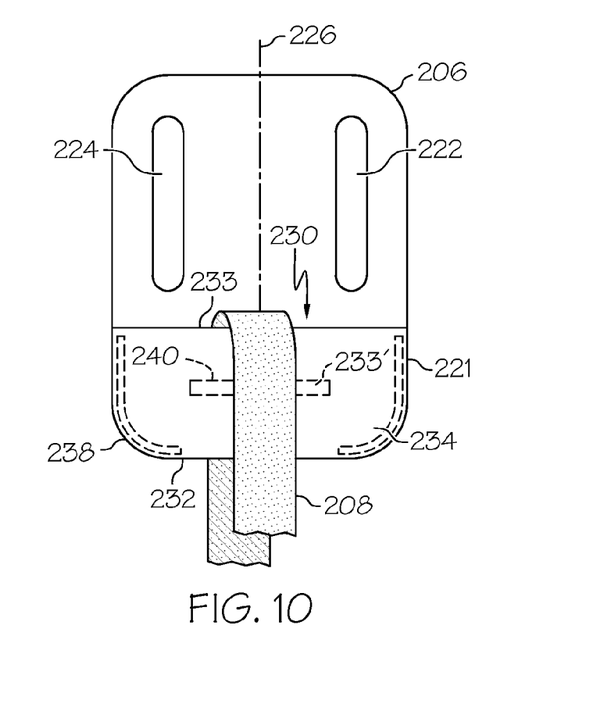
FIG. 10 is a front perspective view of an alternate embodiment of a belt attachment member having a belt therethrough.

In the embodiment illustrated in FIG. 10, an alternate belt attachment member, generally designated 206, is shown that includes a belt entrance 222 and a belt exit 224 oriented generally parallel to the longitudinal axis 226 and a sleeve 221 that defines a strap passage 230 for receiving strap 208. The sleeve 221 may include a front panel 234 superposed on the end 238 of the belt attachment member 206 opposite the belt entrance 222 and belt exit 224. The front panel 234 is attached to the end 238 of the belt attachment member 206 such that it defines a strap entrance 232 and a strap exit 233. The attachment of the front panel 234 to the end 238 of the belt attachment member 206 may be by any connecting means that will retain the panel 234 while supporting the orthosis. The front panel may be sewn, adhered, crimped, molded, rivoted, bolted, or screwed to the end 238 of the belt attachment member 206, but is not limited thereto. Preferably, the strap entrance 232 and the strap exit 233 are positioned opposite one another. In one embodiment, the strap entrance 232 and the strap exit 233 are aligned with the longitudinal axis 226 such that the longitudinal axis of the strap passage 230 is the longitudinal axis 226 of the belt attachment member 206.

In another embodiment, the front panel 234 may include a slot 240 within its interior as the strap exit 233'. Accordingly, the attachment of the front panel 234 to the end 238 of the belt attachment member 206 may extend further around the front panel 234 than the embodiment described above and may not necessarily define a sleeve.

Figure 3:
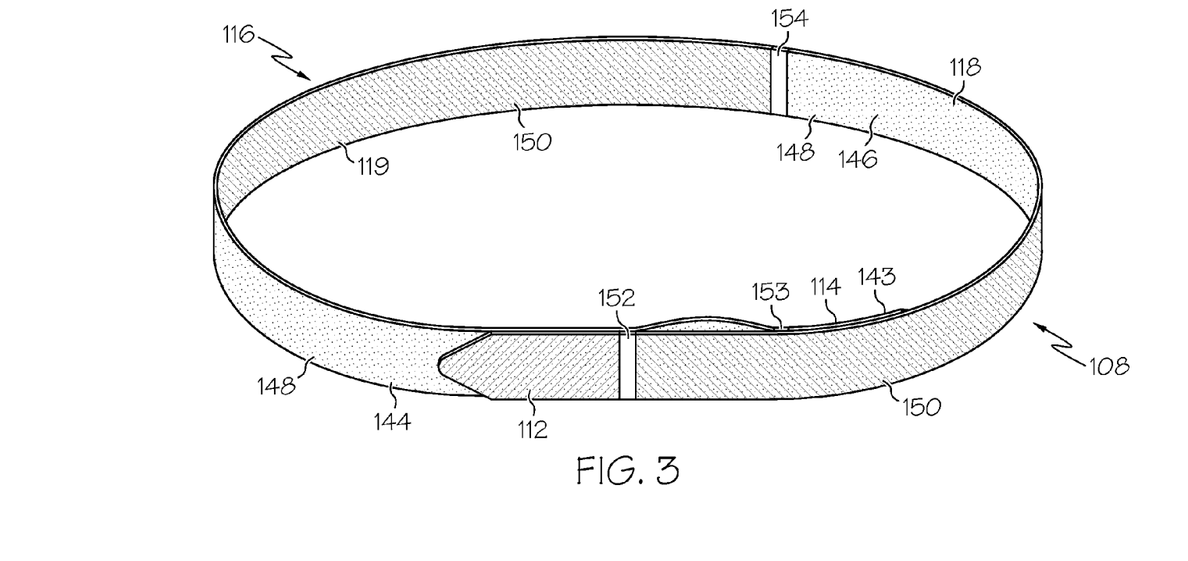
FIG. 3 is a side perspective view of one embodiment of a strap from the orthosis support of FIG. 1 shown as a closed loop.
Figure 4:
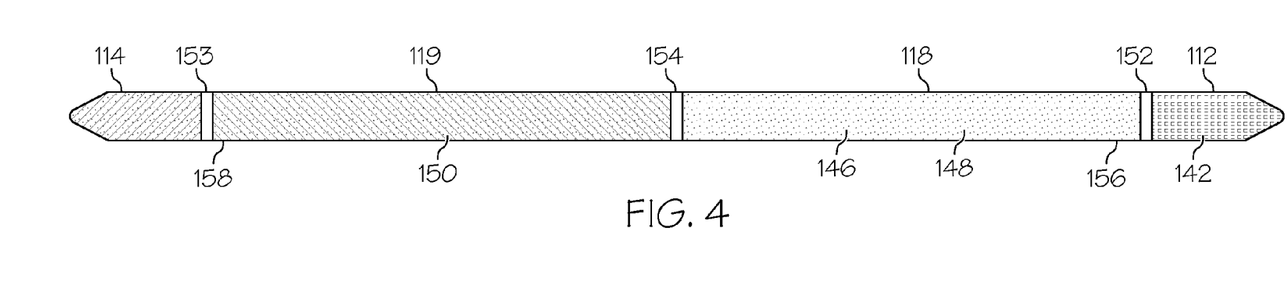
FIG. 4 is a top view of the strap of FIG. 3 lying open.

Now referring to strap 108 illustrated in FIGS. 1-4 and 7-9, the strap 108 is releasably connectable to itself to form a loop. The first end 112 and/or the second end 114 of the strap 108 may include a releasable attachment member 142 and the segment 116 of the strap 108 between the first and second ends 112, 114 includes at least one mating releasable member 144. In one embodiment, best illustrated in FIGS. 3-4, the first end 112 includes a first releasable attachment member 142, the second end 114 includes a second releasable attachment member 143, and the segment 116 includes a first mating releasable member 144 positionable for releasable engagement with the first releasable attachment member 142 of the first end 112 and includes a second mating releasable member 146 positionable for releasable engagement with the second releasable attachment member 143 of the second end 114. The segment 116 between the first and second ends 112, 114 may include two sections 118, 119. Each section 118, 119 has similar first and second major surface, but the two sections 118, 119 are connected to one another such that, when the strap is lying open as illustrated in FIG. 4, the first major surface 148 of the section one 118 faces the same direction, up in FIG. 4, as the second major surface 150 of the section two 119. Accordingly, the two sections 118, 119 may be separate pieces that define a junction 154 where they are connected together. The junction 154 may be or include one or more means of permanently fixing the two pieces together, for example, stitching, adhering, ultrasonic welding, rivets, or combinations thereof. In another embodiment, the segment 116 may be a continuous piece made with at least part of opposite sides thereof having the mating releasable members 144, 146.

In one embodiment, the segment 116 is elastic and the first and second ends 112, 114 are preferably flexible, but non-elastic. The first and second ends 112, 114 may be separate pieces of material connected to the ends 156, 158 of the segment 116. The first end 156 of the segment 116 may be connected to the material defining the first end 112 of the strap. Where the two are connected junction 152 is formed. Similarly, the second end 158 of the segment 116 may be connected to the material defining the second end 114 of the strap. Where these two are connected junction 153 is formed. Both junctions 152, 153 may be or include one or more of a sewn seam, a point of adhesion, an ultrasonic weld, rivets, or other means of permanently fixing the two pieces together. Preferably, the first end 112 is connected to section one 118 with the first releasable member 142 facing the same direction as the second mating releasable member 146, for example, both face up as shown in FIG. 4. Similarly, the second end 114 is connected to section two 119 with the first releasable member 143 facing the same direction as the first mating releasable member 144, but facing the opposite direction as the first end 112 and section one 118. As shown in FIG. 4, the first releasable member 143 of second end 114 and first mating releasable member 144 of section two 119 face down. In another embodiment, the segment 116 and the first and second ends 112, 114 may be a monolithic strap made with the releasable members 142, 143 and the mating releasable members 144, 146 oriented as described above.

In one embodiment, the releasable attachment members 142, 143, for example, are hook-and-loop fastening material (such as VELCRO® fastening material), snaps, and/or hooks to releasably couple the ends 112, 114 of the strap 108 to itself. The segment 116 between the first and second ends 112, 114 includes one or more mating releasable attachment members 144, 146 of the appropriate construction positioned to mate with the releasable attachment members 142, 143. In one embodiment, the first and second ends 112, 114 have the "hook" features of a hook-and-loop fastening material and the segment 116 has the "loop" features of the hook-and-loop fastening material. One of skill in the art will appreciate that the opposite configuration of the hook-and-loop fastening material relative to the first and second ends 112, 114 and the segment 116 will work just as well. In one embodiment, the hook-and-loop fastening material includes a portion thereof that is elastic. Preferably, the loop portion of the hook-and-loop fastening material is elastic and the hook portion is flexible, but non-elastic.

The strap 108, after having one end thereof fed through the strap passage 130, may have either the first end 112 or the second end 114 fed under, over, or around a component of an orthosis and thereafter mated with its respective mating releasable member 144, 146 to form the strap 108 into a closed loop. In one embodiment, the first end 112 of the strap 108 overlaps the portion of the strap 108 having the second end 114 such that at least some part of the first end 112 extends beyond the second end 114, in particular, beyond the junction 153 between the second end 114 and section two 119 so that the first releasable member 142 of the first end 112 is mated with the first mating releasable member 144 of section two 119. In an embodiment where both the first and the second ends 112, 114 include releasable members, once the first end 112 has been overlapped as just described, the second end 114 will overlap the portion of the strap 108 having the first end 112, such that at least some part of the second end 114 extends beyond the first end 112, in particular, beyond the junction 152 of the first end 112 and section one 118 so that the second releasable member 143 of the second end 114 is mated with the second mating releasable member 146 of section one 118. As illustrated in FIG. 3, the first end 112 forms part of the outer major surface of the looped strap and the second end 114 forms part of the inner major surface of the looped strap.

In one embodiment, the first and second ends 112, 114 are of approximately equal length. This is advantageous in providing overlap by both ends 112, 114 onto their respective mating releasable members 144, 146 to provide a closed loop strap and to eliminate any loose ends from being present on the strap that may get caught on something and possibly ripping the strap loose. Sections one and two 118, 119 of the strap 108 may be approximately equal in length, but this is not essential. Accordingly, in one embodiment section one 118 may be longer than section 119 or vice versa. However, both sections 118, 119 should have the mating releasable members 144, 146 positioned adjacent to the junctions formed where each respective section connects to an end of the strap 108. For example, the mating releasable member 144 of section two 119 should be adjacent to junction 153 and may begin at the junction 153 and extend therefrom in a direction away from the second end 114. Similarly, the mating releasable member 146 of section one 118 should be adjacent to junction 152 and may begin at the junction 152 and extend therefrom in a direction away from the first end 112.

One benefit to the orthosis support 100 is its universal application to various wearers and various orthoses. This versatility is related to the presence of the adjustable strap 108 and adjustable belt 102 described above. Accordingly, the orthosis support 100 may be used on patients of different sizes, in particular, of different heights and waist sizes, having different limb lengths, wearing different orthoses, and even orthoses in different positions on the body. The strap 108 as a result of its means for forming a closed loop may be closed to a selected diameter that once the strap 108 extends between the belt attachment member 106 and the orthosis, the strap 108 provides the needed length to support the orthosis.

In one embodiment, the strap 108 may be a 1 in by 29 in strap. In another embodiment, the strap 108 may be a 1 in by 33 in strap. The 29 in strap may be preferable for wearers that are smaller than 5'4" and the 33 in strap may be preferable for wearers 5'4" or taller. These examples are not meant to be limiting.

The embodiments described above and illustrated in the accompanying drawings include embodiments have a single strap 108. However, the orthosis support 100 is not limited there to. In another embodiment, the orthosis support 100 includes a plurality of straps 108. The straps 108 may be received in the same strap passage 130 and/or the belt attachment member 106 may include a plurality of strap passages 130. Depending on the orthosis to be supported a plurality of straps may provide overall greater stability.

While the wearers herein appear in the illustrations of FIGS. 7-9 as humans or models of humans, it is not limited thereto. The orthosis support 100 may be dimensioned appropriately to support an orthosis on an animal.

Although the invention is shown and described with respect to certain embodiments, it should be clear that modifications will occur to those skilled in the art upon reading and understanding the specification, and the present invention includes all such modifications.

What is claimed is:

1. An orthosis support comprising:
    a belt having a connector to close the belt;
    a belt attachment member receiving the belt; and
    a strap extending from the belt attachment member, the strap having a first end and a second end;
    wherein the belt attachment member is movable along the belt;
    wherein the strap, when connected to an orthosis device, is closed as a single, generally continuous loop with at least one of the first and second ends releasably connected to an inside of the strap and the other end releasably connected to the outside of the strap;
    wherein the first end and the second end of the strap both include releasable attachment members and a segment therebetween that includes first and second mating releasable attachment members positionable to mate with the first end and the second end, respectively;
    wherein, when the strap is lying open, the releasable attachment member of the first end faces a first direction opposite a second direction, which the releasable attachment member of the second end is facing;

wherein the segment between the first and second ends includes two sections each having similar first and second major surfaces; wherein the two sections are connected together such that, when the strap is lying open, the first major surface of section one faces the opposite direction as the second major surface of section two; and wherein the open strap has the first releasable attachment member of the first end facing the same direction as the second mating releasable attachment member of section one and the second releasable attachment member of the second end facing the same direction as the first mating releasable attachment member of section two.

2. The orthosis support of claim 1 wherein the belt attachment member includes a belt entrance and a belt exit.

3. The orthosis support of claim 2 wherein the belt attachment member has a longitudinal axis and the belt entrance and belt exit are slots that are generally parallel to the longitudinal axis.

4. The orthosis support of claim 3 wherein the longitudinal axis divides the belt attachment member into two portions; wherein the first portion includes the belt entrance and the second portion includes the belt exit.

5. The orthosis support of claim 2 wherein the belt attachment member comprises a plate that includes a strap passage that the strap passes through; wherein the strap passage, the belt entrance, and the belt exit are all spaced a distance inward from the outer periphery of the plate.

6. The orthosis support of claim 5 wherein the strap passage is a slot oriented generally perpendicular to the belt entrance and belt exit.

7. The orthosis support of claim 1 wherein the belt attachment member includes a sleeve that defines the strap passage.

8. The orthosis support of claim 7 wherein the strap passage is aligned with the longitudinal axis of the belt attachment member.

9. The orthosis support of claim 1 wherein the first end is connected to section one by a first junction, the second end is connected to section two by a second junction, and the two sections are connected by a third junction.

10. The orthosis support of claim 1 wherein the strap is at least partially elastic.

11. The orthosis support of claim 10 wherein the segment between the first and second ends of the strap is elastic.

12. The orthosis support of claim 11 wherein the first and second ends are flexible but non-elastic.

* * * * *